United States Patent
Castellanza et al.

(10) Patent No.: US 11,613,863 B2
(45) Date of Patent: Mar. 28, 2023

(54) DEVICE AND METHOD FOR SIMULATING INJECTIONS OF CEMENT/CHEMICAL MIXTURES INTO SOILS

(71) Applicants: UNIVERSITA' DEGLI STUDI DI MILANO-BICOCCA, Milan (IT); SIREG GEOTECH S.R.L., Arcore (IT); STUDIO ING. ANDREA PETTINAROLI S.R.L., Milan (IT)

(72) Inventors: Riccardo Castellanza, Milan (IT); Stefania Zenoni, Carobbio degli Angeli (IT); Gabriele Balconi, Arcore (IT); Andrea Maria Romildo Pettinaroli, Milan (IT)

(73) Assignees: UNIVERSITÁ DEGLI STUDI DI MILANO-BICOCCA, Milan (IT); SIREG GEOTECH S.R.L., Arcore (IT); STUDIO ING. ANDREA PETTINAROLI S.R.L., Milan (IT)

( * ) Notice: Subject to any disclaimer, the term of this patent is extended or adjusted under 35 U.S.C. 154(b) by 306 days.

(21) Appl. No.: 16/968,841

(22) PCT Filed: Feb. 12, 2019

(86) PCT No.: PCT/IB2019/051120
§ 371 (c)(1),
(2) Date: Aug. 10, 2020

(87) PCT Pub. No.: WO2019/175683
PCT Pub. Date: Sep. 19, 2019

(65) Prior Publication Data
US 2021/0002841 A1  Jan. 7, 2021

(30) Foreign Application Priority Data
Feb. 13, 2018 (IT) .................. 102018000002647

(51) Int. Cl.
*G01N 15/08* (2006.01)
*E02D 1/02* (2006.01)
(Continued)

(52) U.S. Cl.
CPC ............. *E02D 1/025* (2013.01); *E02D 1/027* (2013.01); *E02D 3/12* (2013.01); *G01N 33/24* (2013.01)

(58) Field of Classification Search
CPC .......... G01N 15/08; G01N 33/24; G01N 1/28; G01N 33/246; G01N 15/0806;
(Continued)

(56) References Cited

U.S. PATENT DOCUMENTS

| 2,196,681 | A | * | 4/1940 | Moroney | .................. G01N 1/14 73/863.84 |
| 2,636,689 | A | * | 4/1953 | Fitts | .......................... B02C 4/02 241/230 |

(Continued)

FOREIGN PATENT DOCUMENTS

| DE | 102016110352 | 12/2016 |
| DE | 102016110352 A1 | 12/2016 |

(Continued)

OTHER PUBLICATIONS

International Search Report and Written Opinion for PCT/IB2019/051120 dated May 23, 2019.
(Continued)

*Primary Examiner* — Edwin J Toledo-Duran
(74) *Attorney, Agent, or Firm* — Thomas | Horstemeyer, LLP

(57) ABSTRACT

A device for simulating injections of liquid chemical/cementitious substances into soils, comprising a first observation chamber which delimits an injectable space adapted to accommodate a soil sample, a second observation chamber
(Continued)

which delimits a perforation space adapted to accommodate at least one stretch of an injection device, with longitudinal extension along a longitudinal axis of the second observation chamber, wherein the first observation chamber and the second observation chamber are directly bordering to each other in an interface area, a retaining partition wall which can be inserted in the interface area so as to separate the injectable space from the perforation space and extracted so as to put the perforation space into communication with the injectable space, as well as first transparent portions formed in a first containment wall of the first observation chamber for viewing in real time a propagation of the chemical substance injected into the soil sample by means of the injection device. A method comprising a step of simulating by the device.

22 Claims, 9 Drawing Sheets

(51) Int. Cl.
*E02D 3/12* (2006.01)
*G01N 33/24* (2006.01)

(58) Field of Classification Search
CPC .......... E02D 1/025; E02D 1/027; E02D 3/12; G01B 21/02; G01B 21/32
See application file for complete search history.

(56) References Cited

U.S. PATENT DOCUMENTS

| | | | | |
|---|---|---|---|---|
| 2,656,718 A * | 10/1953 | Dames | G01N 3/24 | 346/50 |
| 2,746,731 A * | 5/1956 | Chu | G01N 33/24 | 73/61.41 |
| 2,779,195 A * | 1/1957 | Simon | E21B 25/08 | 175/49 |
| 2,824,445 A * | 2/1958 | Reese | E02D 1/022 | 73/790 |
| 2,913,897 A * | 11/1959 | Kirkham | G01N 33/24 | 73/38 |
| 2,923,148 A * | 2/1960 | Kirkham | E02D 1/00 | 239/74 |
| 2,993,367 A * | 7/1961 | Fletcher | E02D 1/022 | 73/843 |
| 3,216,242 A * | 11/1965 | Eyrich | G01N 33/24 | 73/823 |
| 3,457,777 A * | 7/1969 | Nielsen | G01N 3/08 | 73/84 |
| 3,499,320 A * | 3/1970 | Fox | E21B 49/006 | 73/152.02 |
| 3,572,997 A * | 3/1971 | Burk | G01N 33/24 | 206/568 |
| 3,608,367 A * | 9/1971 | Karol | G01N 15/0806 | 73/823 |
| 3,708,319 A * | 1/1973 | Eilers | E21F 5/18 | 106/900 |
| 3,769,581 A * | 10/1973 | Konig | G01V 3/06 | 73/32 R |
| 3,820,385 A * | 6/1974 | Cordoba | G01N 3/08 | 73/84 |
| 3,872,717 A * | 3/1975 | Fox | E02D 1/022 | 73/84 |
| 3,914,993 A * | 10/1975 | Babcock | G01L 1/2218 | 73/767 |
| 3,924,451 A * | 12/1975 | Drnevich | G01N 33/24 | 73/594 |
| 3,934,455 A * | 1/1976 | Harrisberger | G01N 15/082 | 436/25 |
| 3,962,915 A * | 6/1976 | Jezequel | E21B 49/006 | 73/152.54 |
| 4,024,758 A * | 5/1977 | Latimer | G01C 25/00 | 73/170.32 |
| 4,047,425 A * | 9/1977 | Handy | G01N 3/08 | 73/822 |
| 4,192,963 A * | 3/1980 | Koehmstedt | H02G 9/00 | 405/265 |
| 4,400,970 A * | 8/1983 | Ali | E02D 1/022 | 73/9 |
| 4,483,197 A * | 11/1984 | Kellner | G01N 17/00 | 73/150 R |
| 4,554,819 A * | 11/1985 | Ali | G01N 3/00 | 73/9 |
| 4,579,003 A * | 4/1986 | Riley | G01N 33/24 | 73/807 |
| 4,594,899 A * | 6/1986 | Henke | E02D 1/022 | 73/152.59 |
| 4,956,993 A * | 9/1990 | Mehler | G01N 15/08 | 73/38 |
| 5,038,040 A * | 8/1991 | Funk | A01C 21/007 | 250/341.8 |
| 5,191,787 A * | 3/1993 | Hanson | G01N 33/24 | 73/86 |
| 5,203,824 A * | 4/1993 | Henke | E21B 11/005 | 175/203 |
| 5,243,850 A * | 9/1993 | Hanson | G01N 33/24 | 73/86 |
| 5,594,185 A * | 1/1997 | Winberry | G01N 33/246 | 73/863.52 |
| 5,920,005 A * | 7/1999 | Moss | G01N 3/24 | 73/9 |
| 5,974,899 A * | 11/1999 | Hanks | G01N 1/34 | 73/866 |
| 6,125,948 A * | 10/2000 | David | E21B 49/02 | 73/864.45 |
| 6,138,590 A * | 10/2000 | Colburn, Jr. | A01C 23/02 | 47/1.3 |
| 6,324,922 B1 * | 12/2001 | Hanks | G01N 1/34 | 73/866 |
| 6,349,590 B1 * | 2/2002 | Wai | E02D 33/00 | 73/84 |
| 6,431,006 B1 * | 8/2002 | Henke | G01N 3/40 | 73/843 |
| 6,938,461 B1 * | 9/2005 | Johnson | E21B 49/00 | 73/37 |
| 9,453,829 B2 * | 9/2016 | Feng | E02D 1/025 | |
| 9,606,087 B1 * | 3/2017 | Taylor | G01N 33/24 | |
| 9,625,438 B1 * | 4/2017 | El-Sheikhy | G01B 21/02 | |
| 10,809,175 B1 * | 10/2020 | Ayadat | G01N 15/0826 | |
| 2002/0057944 A1 * | 5/2002 | Adams | B01D 17/0208 | 405/39 |
| 2003/0162303 A1 * | 8/2003 | Soni | G01N 33/24 | 422/534 |
| 2005/0191758 A1 * | 9/2005 | Pether | G01N 3/12 | 422/68.1 |
| 2012/0002192 A1 * | 1/2012 | Preiner | G01N 21/33 | 356/51 |
| 2013/0055797 A1 * | 3/2013 | Cline | G01N 3/303 | 73/82 |
| 2013/0200905 A1 * | 8/2013 | Rhodes | G01N 33/246 | 324/667 |
| 2015/0033842 A1 * | 2/2015 | Bergendahl | E02D 1/022 | 73/152.59 |
| 2015/0197908 A1 * | 7/2015 | Puppala | E02D 1/022 | 324/696 |
| 2015/0267370 A1 * | 9/2015 | Gupta | E02D 1/027 | 73/818 |
| 2015/0268217 A1 * | 9/2015 | Gupta | G01N 33/24 | 73/819 |
| 2015/0316526 A1 * | 11/2015 | Kimmel | E02D 1/022 | 73/818 |
| 2015/0377853 A1 * | 12/2015 | Feng | G01N 15/08 | 73/863 |
| 2016/0054211 A1 * | 2/2016 | Li | G01N 3/08 | 73/818 |
| 2016/0356685 A1 * | 12/2016 | Gupta | G01N 3/08 | |
| 2017/0227537 A1 * | 8/2017 | Guo | G01N 33/56988 | |

(56) References Cited

U.S. PATENT DOCUMENTS

| | | | | |
|---|---|---|---|---|
| 2019/0082612 A1* | 3/2019 | Bitetti | .................... | A01G 7/045 |
| 2019/0128792 A1* | 5/2019 | Roth | .................... | G01N 15/082 |
| 2019/0154566 A1* | 5/2019 | Ast | .................... | A61B 5/7225 |
| 2019/0376251 A1* | 12/2019 | Tan | .................... | G01N 3/24 |
| 2021/0122503 A1* | 4/2021 | Cho | .................... | G01N 3/60 |
| 2021/0364401 A1* | 11/2021 | Guo | .................... | G01N 3/08 |
| 2022/0146387 A1* | 5/2022 | Ling | .................... | G01N 3/18 |

FOREIGN PATENT DOCUMENTS

| | | |
|---|---|---|
| WO | 2013125965 | 8/2013 |
| WO | 2013125965 A2 | 8/2013 |

OTHER PUBLICATIONS

International Search Report for PCT/IB2019/051120 dated May 23, 2019.

* cited by examiner

DEVICE AND METHOD FOR SIMULATING INJECTIONS OF CEMENT/CHEMICAL MIXTURES INTO SOILS

CROSS-REFERENCE TO RELATED APPLICATIONS

This application is the 35 U.S.C. § 371 national stage application of PCT application PCT/IB2019/051120, filed Feb. 12, 2019, where the PCT claims the priority to and benefit of Italian Patent Application No. 102018000002647, filed Feb. 13, 2018, both of which are hereby incorporated by reference in their entireties.

DESCRIPTION

The present invention relates to a device and method for simulating injections of cement and chemical mixtures into soils in order to modify the properties thereof, in particular injections of cement/chemical mixtures with soil reinforcement purposes by creating inter-granular bonds which increase the resistance thereof, e.g. when preparing for digging a tunnel to prevent collapse or deformation of the soil during excavation of tunnels or trenches, and/or to modify soil permeability (impermeabililization), soil bearing capacity (consolidation), to provide underpinning and hydraulic soil stabilization interventions (anti-siphoning) and to clog porosities, cracks and fractures in rock formations.

In order to stabilize the ground in preparation and while excavation, it is known to make a series of perforations having predefined directions, depth and distances on the basis of an often empirical geotechnical engineering project, wherein injection pipes, named grouting pipes, are inserted in the perforations; these are laid into the ground by forming a cement sheath (possibly also by means of the pipes themselves) outside the pipe which fills the inside of the hole up to its head. The injection around the perforation is performed, in selective and localized manner, by means of the grouting pipes according to the requirements of the geotechnical engineering project In practice, a single grouting pipe is inserted into each perforation, through which a first injection of a cement mixture can occur for making the so-called outer sheath, which extends along the annular space comprised between the hole in the ground and the grouting pipe. For such filling, which can be performed also by means of the pipe valves, a cement mixture containing bentonite is usually used, the rheological properties of which provide plasticity to the sheath, which also has the function of containing the wall of the hole. During perforation and injection of the sheath, it may be necessary to prevent the instability of the wall of the hole by using an external steel lining pipe, which, during the making of the bentonite sheath, is gradually pulled upwards and finally removed completely from the perforation. At that point, the support function of the wall of the hole is performed by the bentonite plastic sheath.

Subsequently, one or more selective treatment injections are performed, localized along the extension of the grouting pipe, in the positions and by means of the chemical/cement mixtures substances prescribed by the subsoil treatment geotechnical-engineering project.

The injections are treated by conveying the chemical/cement substance at pressure, flow rate and total volume prescribed by the geotechnical-engineering project and/or possibly determined empirically on-site. This occurs by means of the grouting pipe through one valve at a time, in selected locations, so for the chemical/cement liquid, injected at a given pressure, breaks and locally crosses the bentonite plastic sheath and locally penetrates in the surrounding soil to modify its properties in the desired manner.

During the injection treatment, the bentonite sheath prevents unwanted spilling along the perforation of the mixture being injected, ensuring instead an infiltration of the soil surrounding the valve, in prevalently radial direction with respect to the longitudinal extension of the perforation into the soil and of the grouting pipe inserted therein.

Grouting pipes used for injection are known. They comprise one or more tubular elements, e.g. made of plastic material, which can be connected to one another by means of threaded connections to form a pipe of the desired length. The pipe is provided with one or more injection valves arranged in discrete positions along one or more of pipe elements (where necessary).

Typically, each injection valve consists of a group of small holes, e.g. four, in radial position, obtained with a constant diameter in the wall of the tubular element, preferably spaced at constant pitch along the circumference of the tubular element itself; externally, they are surrounded and covered by an elastic and expandable sleeve, of limited length, e.g. 10 cm, the so-called "manchette" or "hose". The hose is inserted on the tubular segment above the through holes, roughly straddling them, and may be retained in position by two, substantially rigid rings. The hose is elastically expandable by the effect of the pressure of the injected fluid, which is injected through the small holes and, by virtue of the presence of the hose, flows along the gap between the tubular element and the dilated hose itself until it interacts with the bentonite plastic sheath and then with the surrounding soil.

For the targeted conveying of the chemical/cement liquid to the selected injection valve a single or double expansion shutter, named "packer", also known, is usually used, which can be inserted into and removed from the grouting pipe and which comprises one or two expandable portions against the inner surface of the grouting pipe in order to hydraulically isolate a stretch of the grouting pipe, i.e. the one delimited between the two expandable portions or between an expandable portion and a closed end of the grouting pipe. The expansion shutter is connected to a pipe which can be connected to a pump; the latter, by means of such pipe, sends pressurized chemical/cement liquid to be injected, until the shutter, which releases the mixture into the isolated pipe segment isolated by means of one or the two expandable portions of the packer.

Because of the heterogeneous nature of soils, as well as the difficulty of execution of widespread geological research and of the respective costs, the properties of the subsoil, such as for example granulometric composition, permeability (or hydraulic conductivity), relative density, water saturation degree, emptiness index and mechanical properties which characterize a soil consolidation geotechnical-engineering project, differ from case to case even greatly. This implies a certain difficulty in defining, at the design stage, parameters and injection mixtures optimized for every single intervention, with a consequent tendency to adopt a very conservative approach to design or sometimes, on the contrary, to underestimate the effect of the treatments.

As a consequence of this, many geological-engineering projects are still now dealt with empirical methods, and can be improved with respect to the definition of the more appropriate treatment mixtures, the injection parameters (distance between perforations, vertical and horizontally distances between injection points, injection pressure, total injection volume, maturation intervals between two consecutive injection cycles) and therefore often lead to treatment costs assessed in inappropriate manner.

Soil injection process simulation is a promising way to optimize geological-engineering projects and subsoil injection performance. However, until today, numerical simulation attempts do not provide satisfactory results for a lack of certainty of the input parameters for numerical modeling the mechanical and fluid-dynamic process by means of discrete elements, boundary elements and finite elements.

Experimental simulation in situ by means of test injections in the concerned area provides more reliable results than numerical simulation. However, it requires setting up an appropriate site in the intervention area (with consequent installation and securing of the area) to perform a test field of e.g. 10 by 10 meters. This requires the installation and use of the equipment needed to perform the injections, followed by a series of surveys and analysis of the subsoil volume subjected to injection. All this implies very high costs, with great difficulty and low cost-effectiveness in repeating the simulation several times varying parameters and mixtures, whereby compromising injection process optimization. Furthermore, such test fields, precisely for the burdens described above, are generally performed only at the beginning of the works, rather than while defining the executive project, which would be conceptually correct.

Last but not least, the experimental simulation in situ only makes it possible to ascertain the results of the experimentation after the injection has already completed and after a curing period of the experimentally injected soil, with no possibility of directly observing the injection process in real time in the soil.

It is thus the object of the present invention to provide a device and an experimental simulation method of injections of chemical/cement mixtures into soils, having features such to solve at least some of the drawbacks mentioned with reference to the prior art.

It is a particular object of the invention to provide a device and an experimental simulation method of injections of chemical/cement mixtures into soils, having features such as to allow the observation, and possibly the detection of phenomena and significant quantities of the injection process in real time during the injection and in the curing intervals between consecutive injections.

It is a further particular object of the invention to provide a device and an experimental simulation method of injections of chemical/cement mixtures into soils, having such features as to allow a higher and varied number of simulations, necessary for project optimization, at low cost.

Further objects of the invention are to provide:
a method for defining or optimizing a geotechnical-engineering project for the treatment/consolidation of a soil comprising the simulation method,
a method for executing a soil treatment/consolidation comprising the simulation method,
a numerical simulation method of soil injection processes by means of a finite element model, comprising a step of determining input parameters (numerical model parameter calibration) by means of the experimental simulation method.

These and other objects are achieved by a device for simulating injections of liquid chemical/cement mixtures in soils according to claim 1.

Dependent claims relate to preferred and advantageous embodiments.

According to an aspect of the invention, a device for simulating injections of liquid chemical substances in soils comprises:
a supporting structure,
a first observation chamber which delimits an injectable space adapted to accommodate a soil sample,
a second observation chamber which delimits a perforation space adapted to accommodate at least one stretch of an injection device for injecting chemical substances, e.g. a grouting pipe, with longitudinal extension along a longitudinal axis of the second observation chamber,
wherein the first and second observation chamber are connected to the support structure and are directly bordering to each other in an interface area,
wherein the first observation chamber extends from the interface area in radial direction with respect to the longitudinal axis, and is delimited by a first containment wall, and
wherein the second observation chamber extends from the interface area in direction opposite to the extension of the first observation chamber, and is delimited by a second containment wall,
a retaining partition wall:
a position inserted in said interface area so as to separate the injectable space from the perforation space and to prevent the falling of material of the soil sample from the first observation chamber into the second observation chamber, and
a position extracted out of the interface region so as to put the perforation space into communication with the injectable space in the interface area,
one or more first transparent portions formed in the first containment wall and extending from a connecting area between the first observation chamber and the second observation chamber away from the longitudinal axis for viewing in real time a propagation of the chemical substance injected into the soil sample by means of the injection device.

The simulation device thus configured allows an experimental simulation of injection processes of soils in conditions very close to reality, with reduced dimensions, with the possibility of verification by viewing in real time, as well as with ease of repetition and variation of types of fluids and injection parameters at low cost.

According to an embodiment, the first transparent portions are configured and positioned for a direct viewing to the naked eye or by means of cameras from the outside of the first observation chamber.

Additionally or alternatively, indirect viewing display devices, e.g. one or more cameras, optical sensors or spectrometers, can be associated with the first transparent portions.

According to a further aspect of the invention, a method for simulating injections of liquid chemical substances into soils comprises:
preparing a soil sample having chosen properties,
placing the soil sample in the first observation chamber of the simulation device, e.g. with known density features and water content,
preparing an injection device, e.g. a grouting pipe, having chosen properties,
installing the injection device in the second observation chamber of the simulation device,
carrying out an injection program of the chemical/cement substance by means of the injection device installed in the second observation chamber,
viewing in real time a propagation of the chemical/cement substance injected by means of the injection device in the soil sample, through the one or more first transparent portions of the containment wall of the first observation chamber.

According to embodiments, the viewing may comprise a direct viewing to the naked eye or by means of cameras from the outside of the first observation chamber or an indirect viewing by means of indirect viewing devices, e.g. one or more cameras, optical sensors or spectrometers associated with the first transparent portions.

In order to better understand the invention and appreciate its advantages, some non-limiting examples of embodiments will be described below with reference to the accompanying figures, in which.

Figure 1:
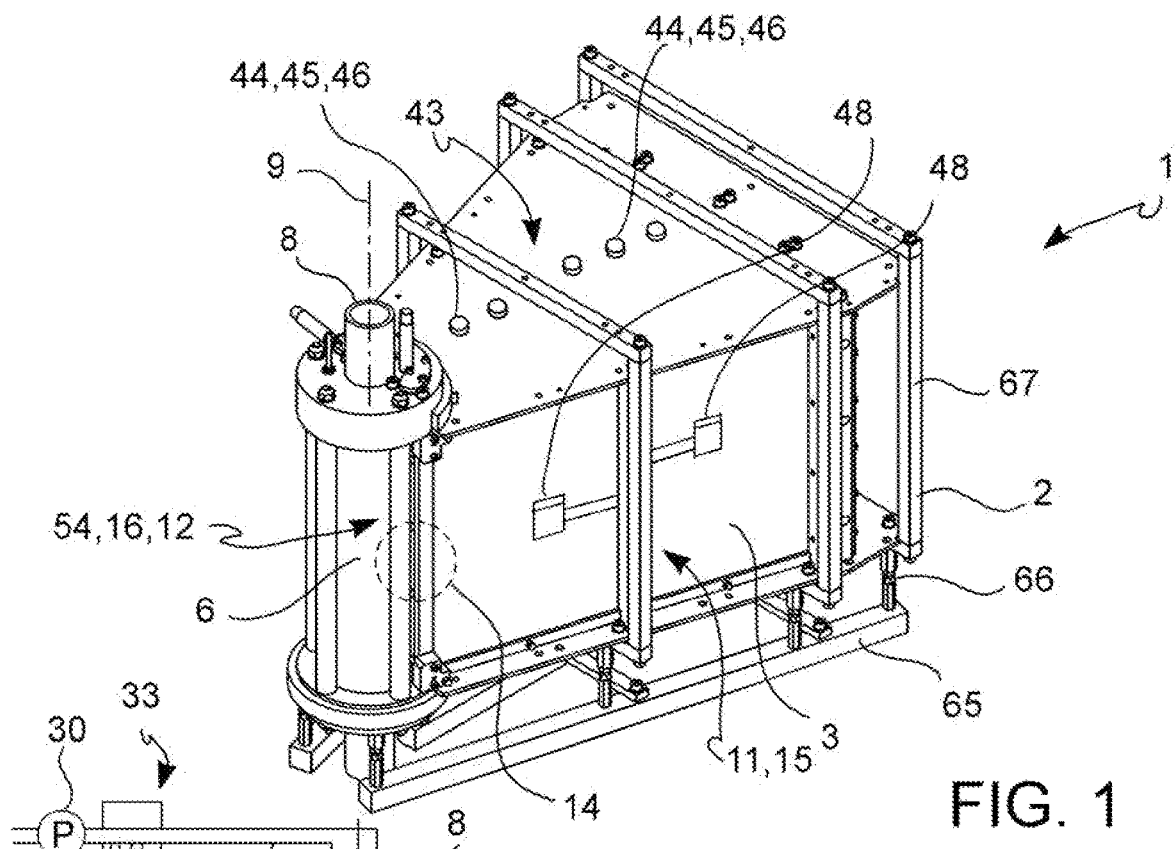
FIGS. 1 and 2 are perspective views of a device for experimentally simulating injections of chemical/cement substances into soils according to an embodiment.
Figure 2:
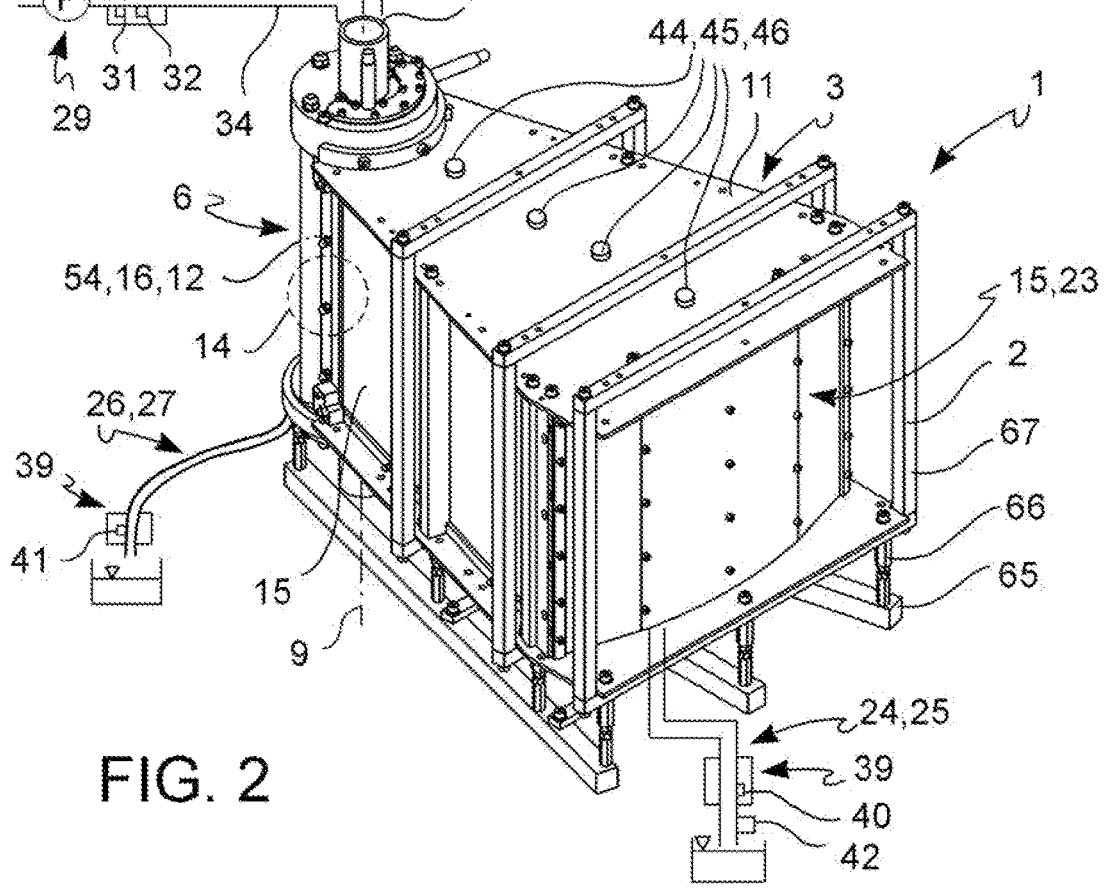
Figure 3:
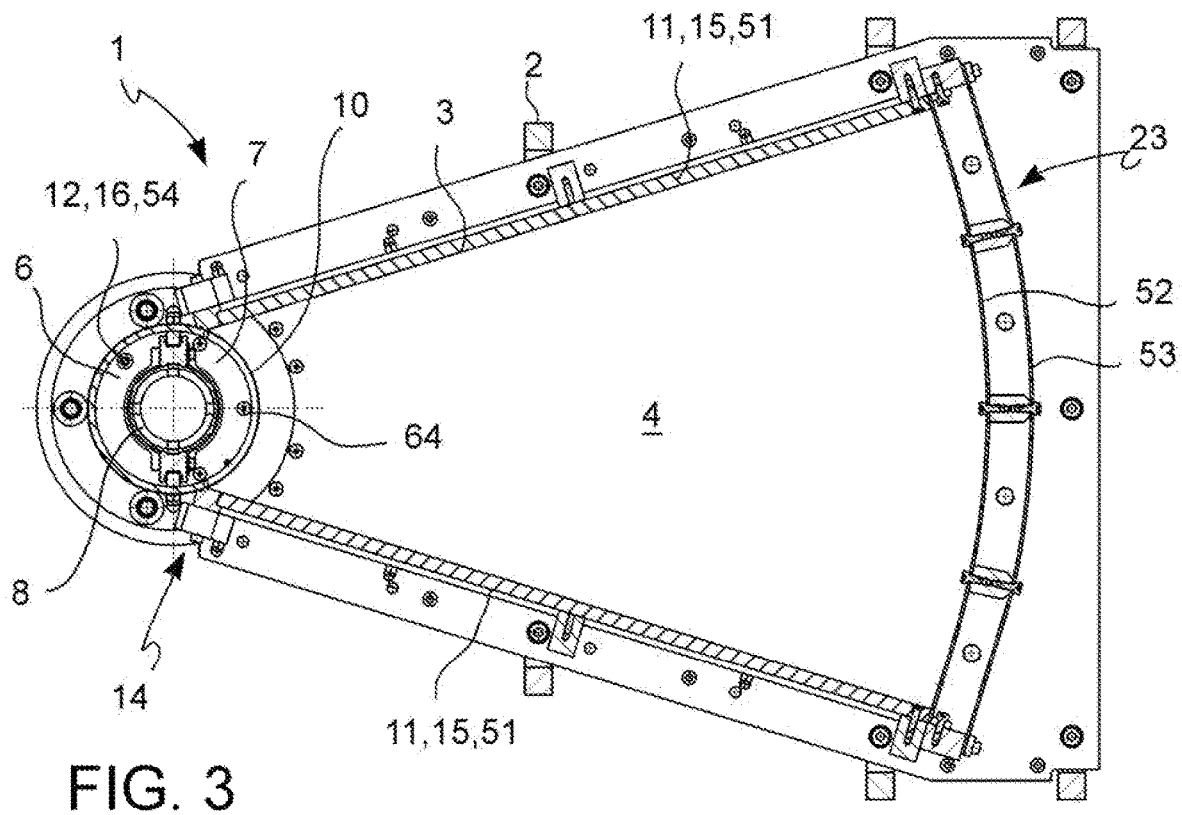
FIG. 3 is a horizontal section view of the device in FIG. 1.
Figure 4:
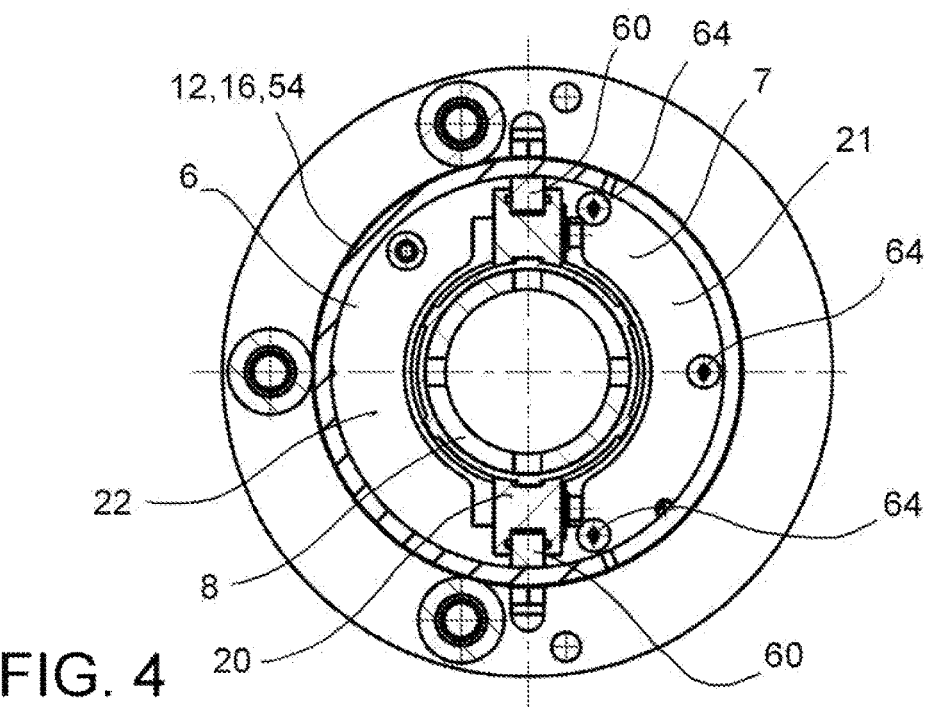
FIG. 4 is an enlarged horizontal section view of a second observation chamber of the simulation device, with an injection device installed, according to an embodiment of the invention.
Figure 5:
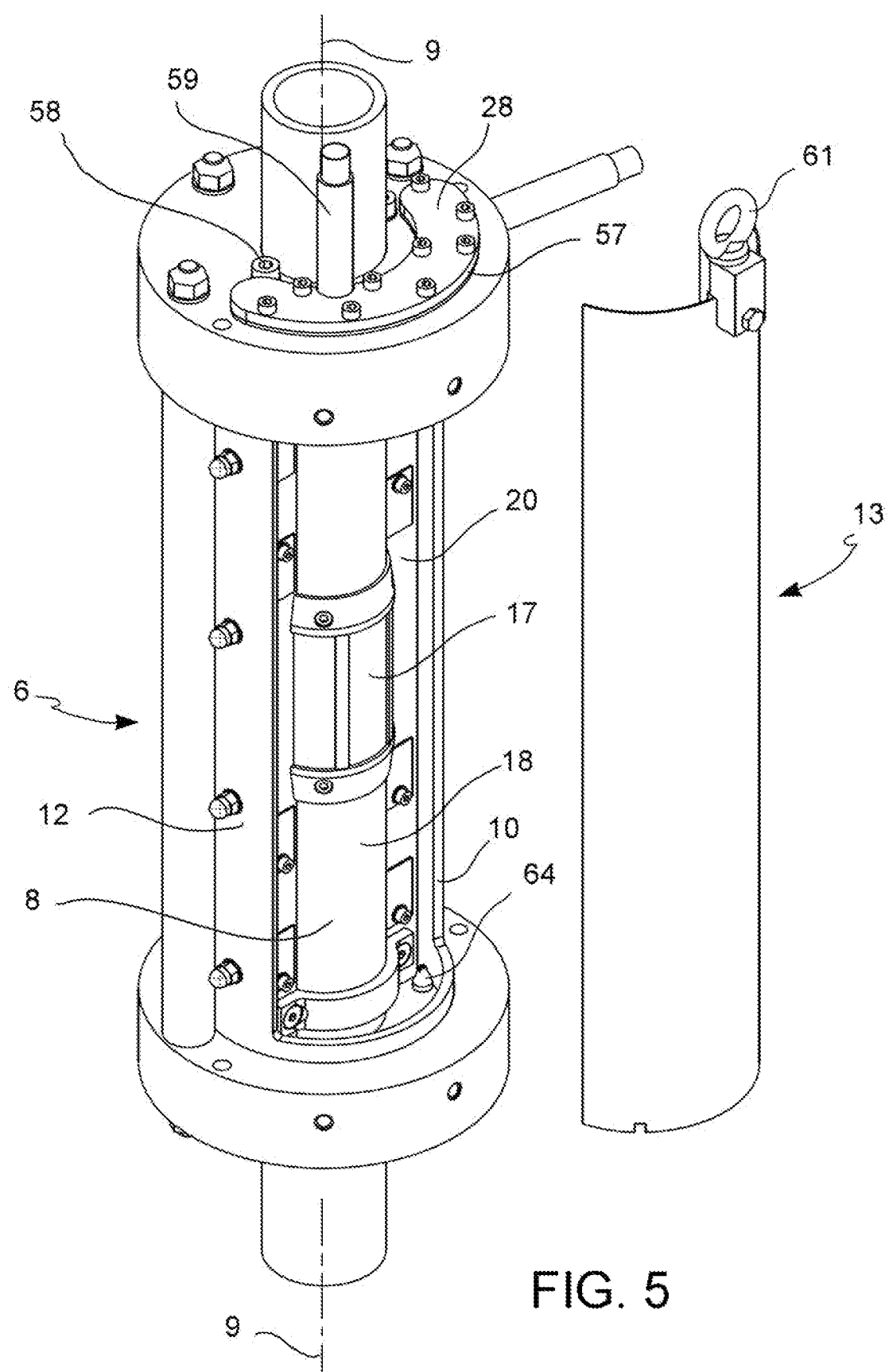
FIG. 5 is a perspective view of a second observation chamber of the simulation device, with an injection device installed and with a retaining partition wall, according to an embodiment of the invention.
Figures 6, 7:
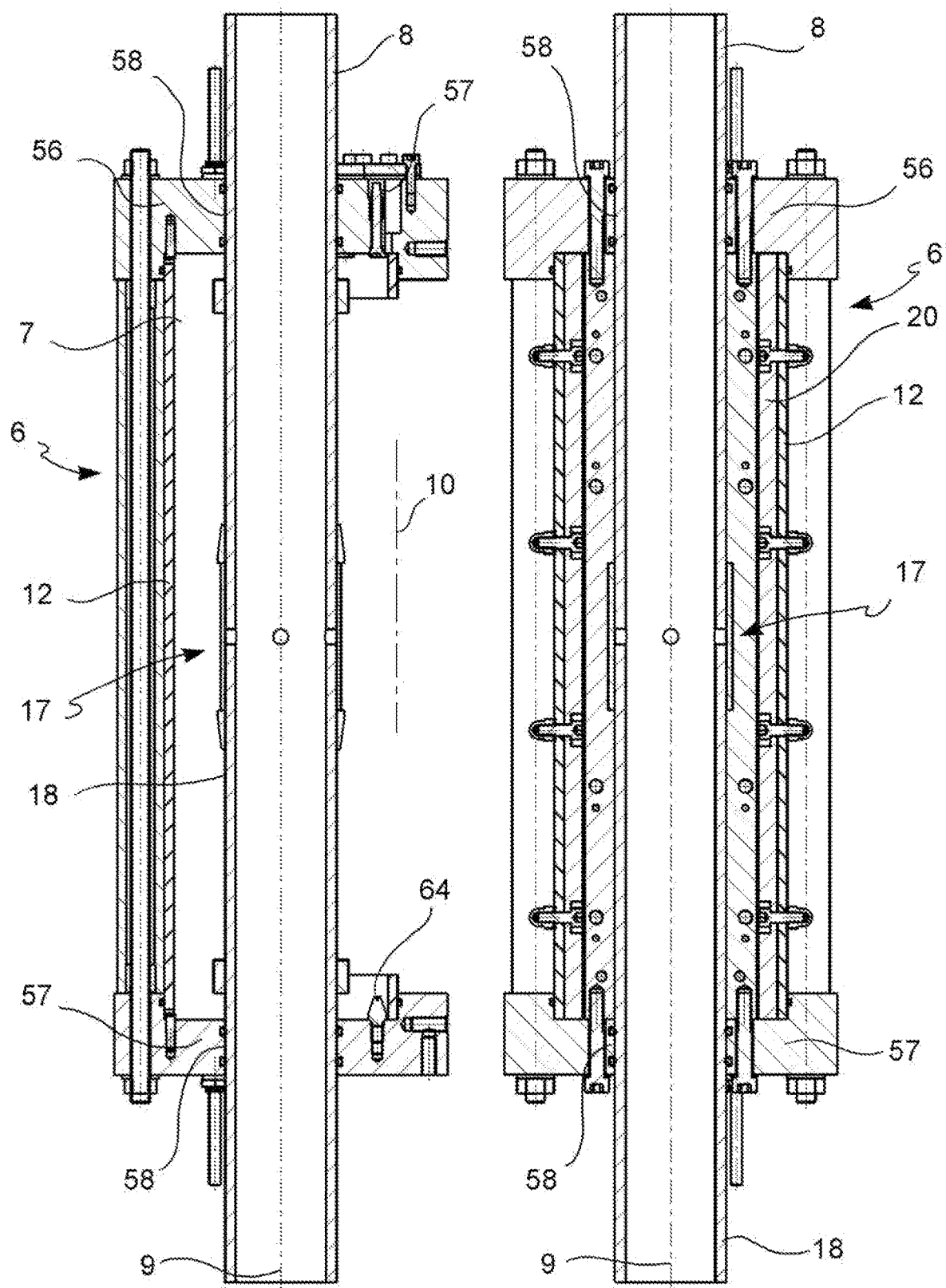
FIGS. 6 and 7 show the second observation chamber of FIG. 5 in a sectional view according to two mutually perpendicular sectional planes radial to a longitudinal axis of the first observation chamber according to an embodiment.
Figure 9:
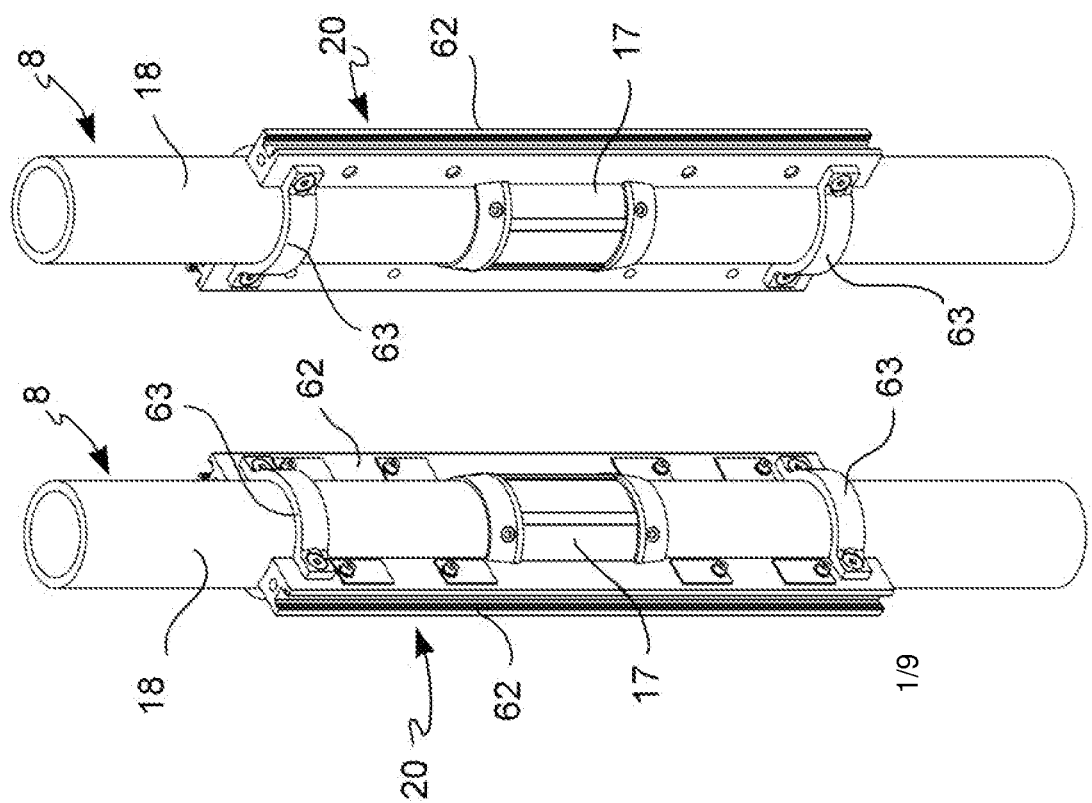
FIG. 9 shows the grouting pipe with a division partition of the first observation chamber of the simulation device, in pre-assembled configuration.
Figure 8:
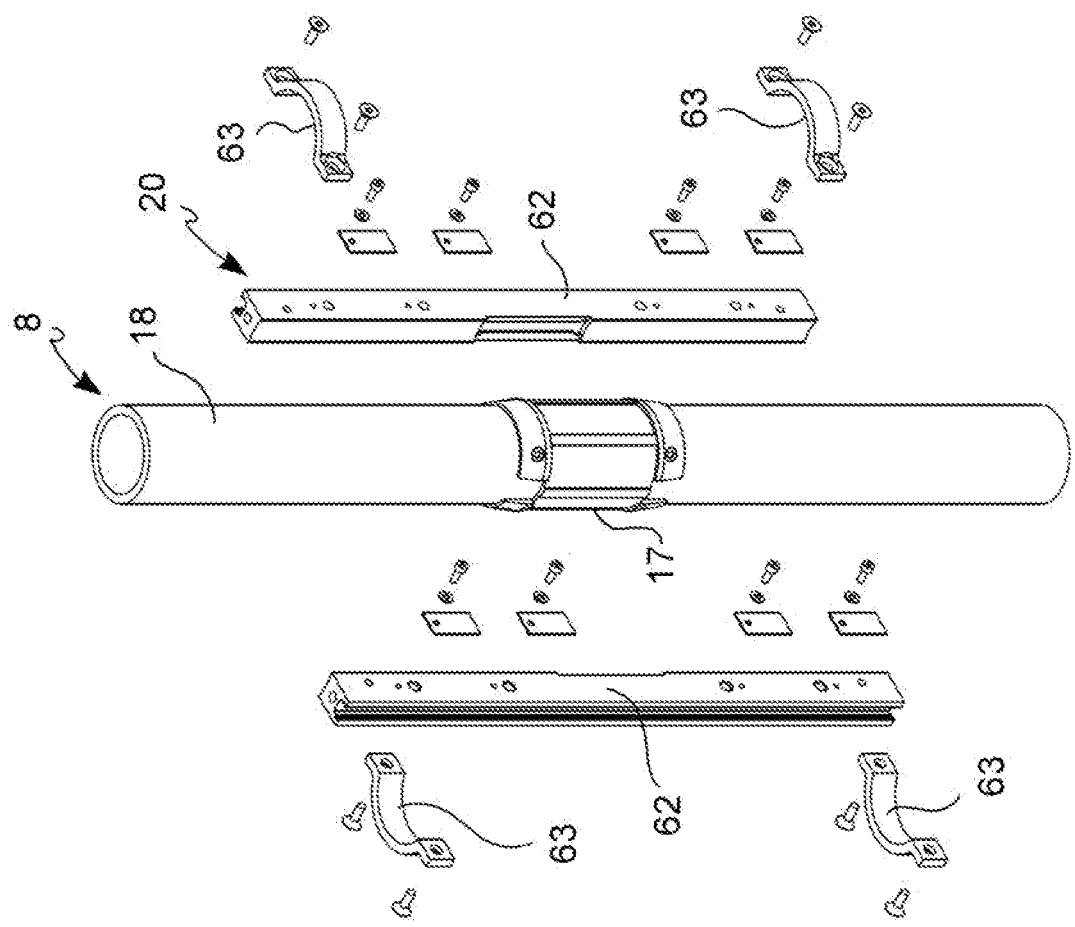
FIG. 8 shows a grouting pipe together with a division partition of the first observation chamber of the simulation device, in its disassembled configuration.
Figure 10:
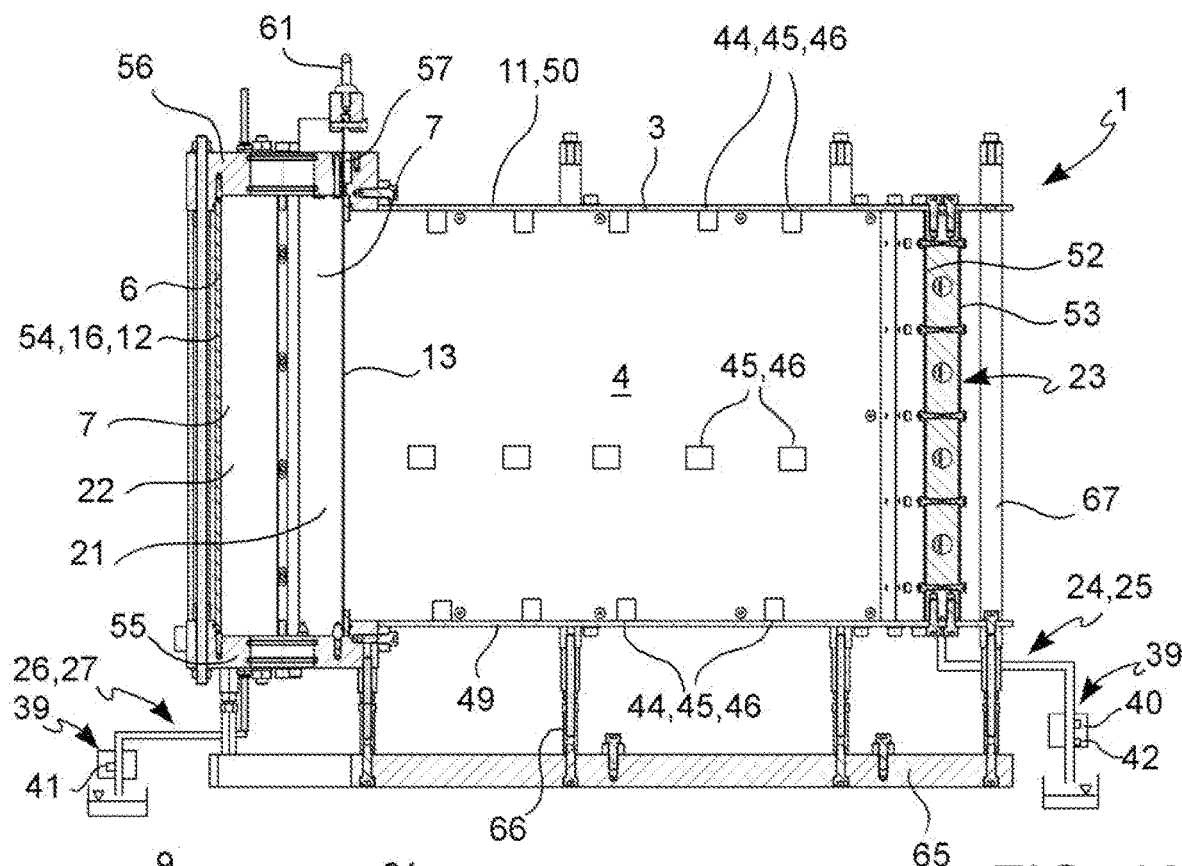
Figure 11:
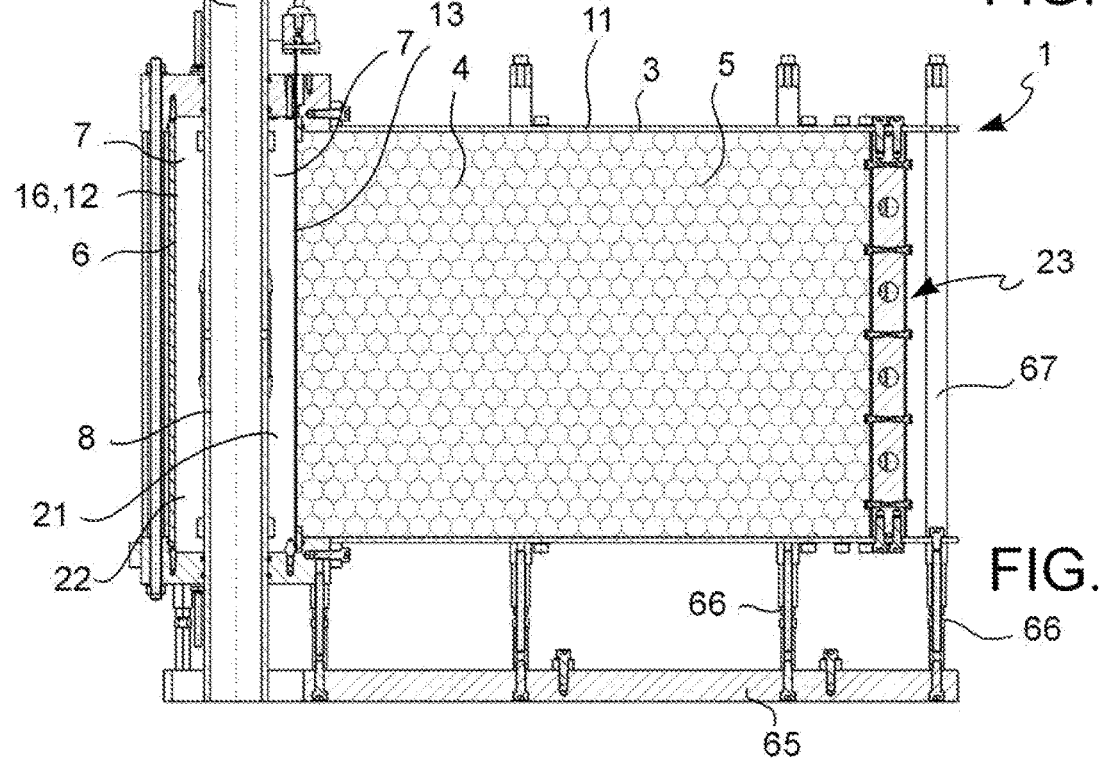
Figure 12:
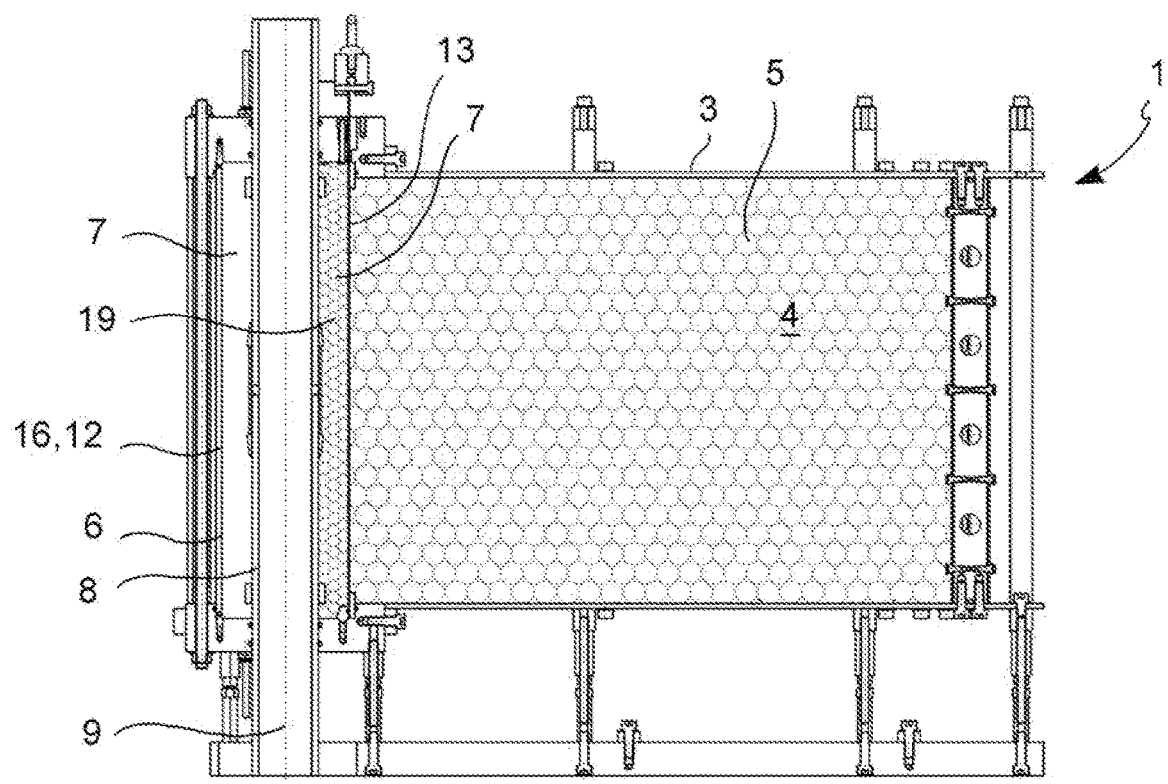
Figure 13:
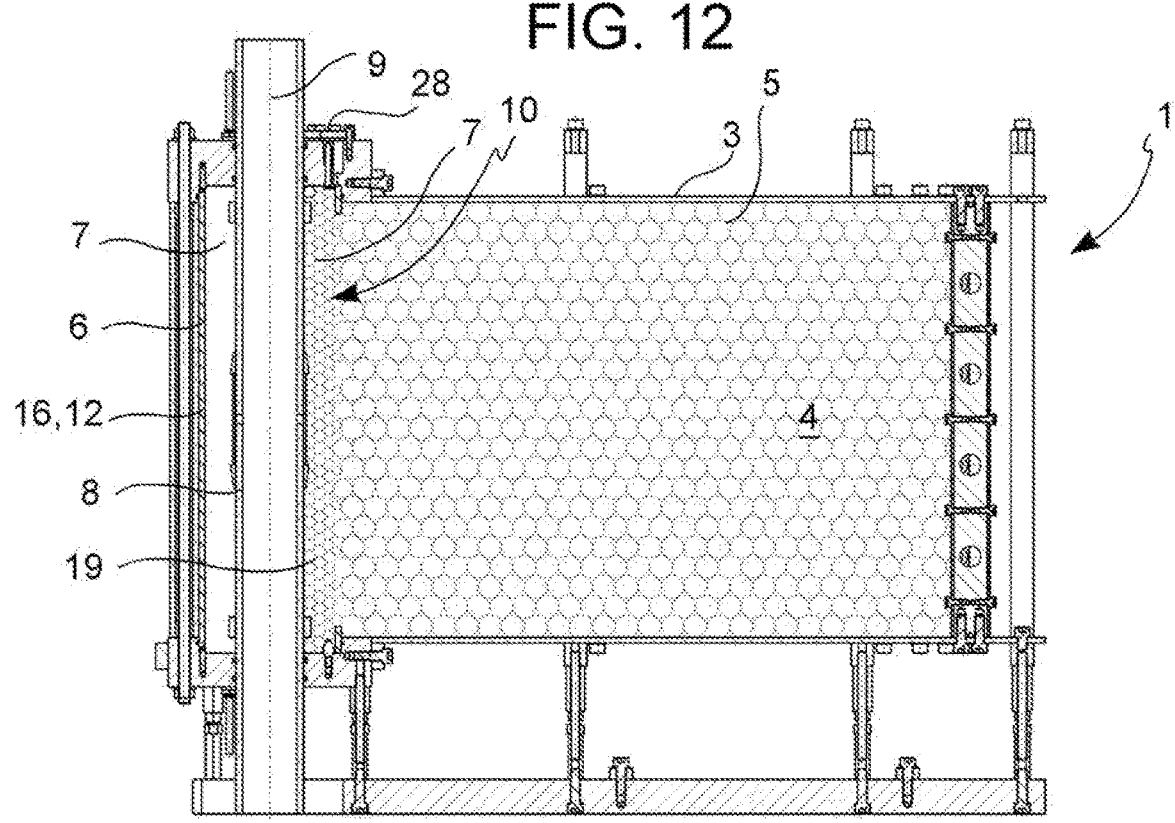
Figure 14:
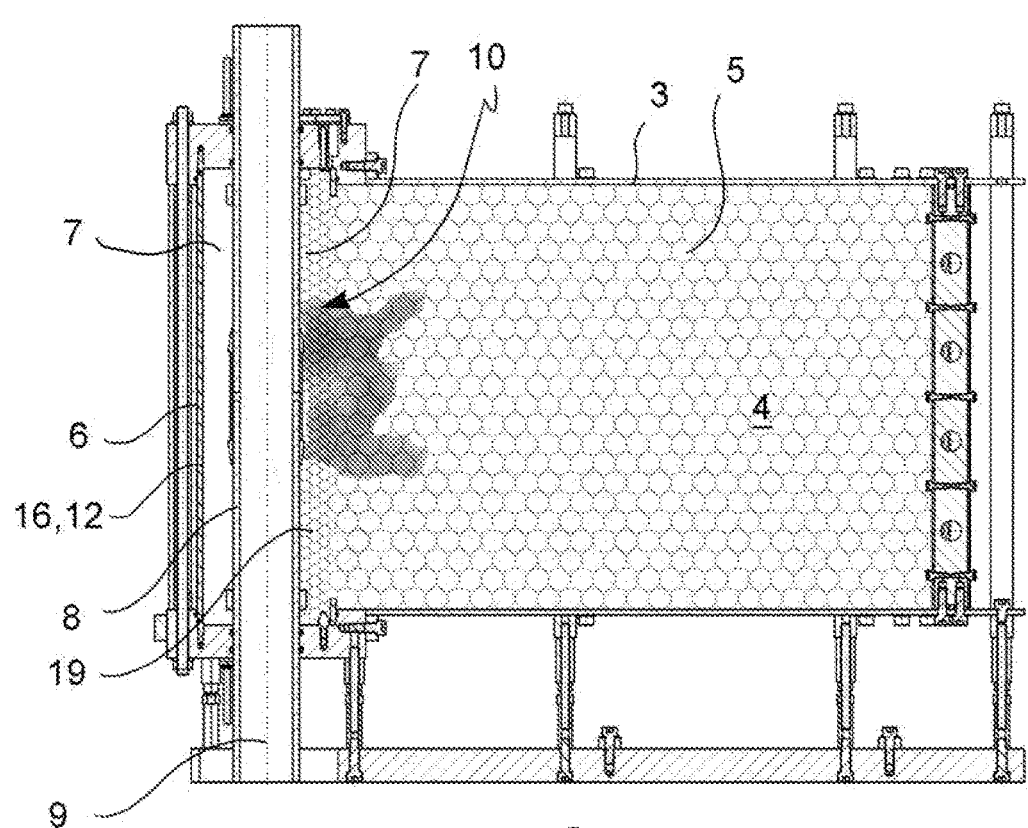
Figure 15:
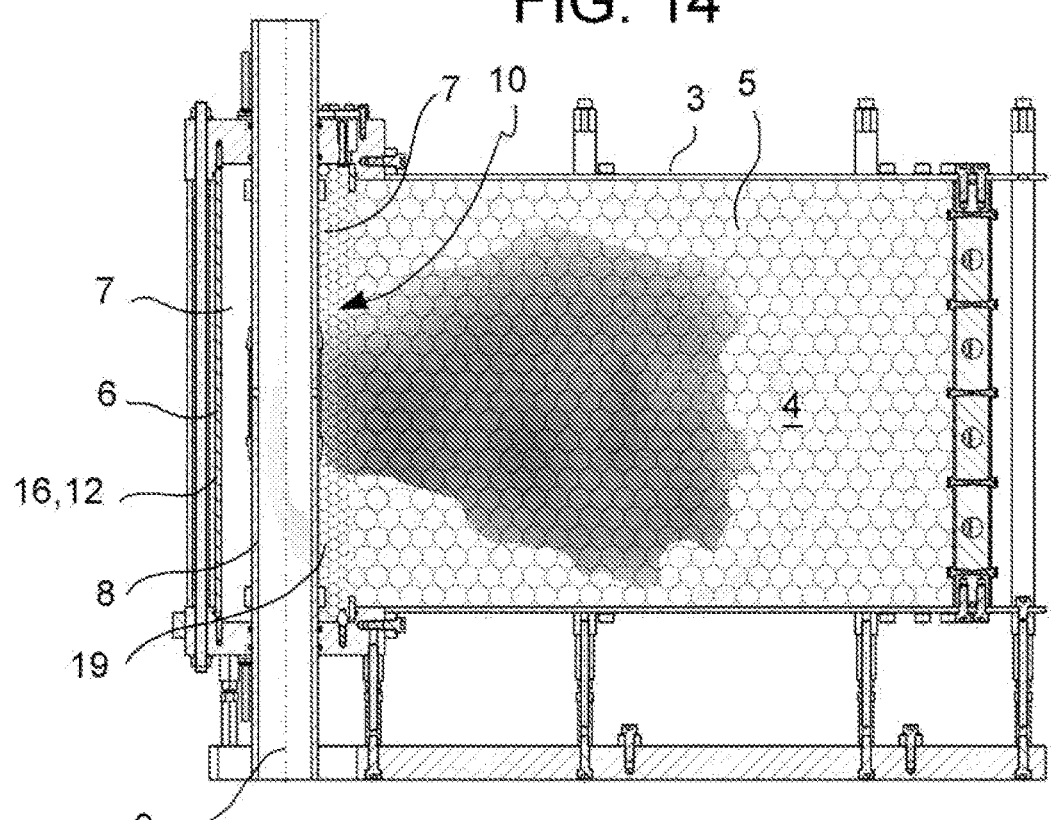
Figure 16:
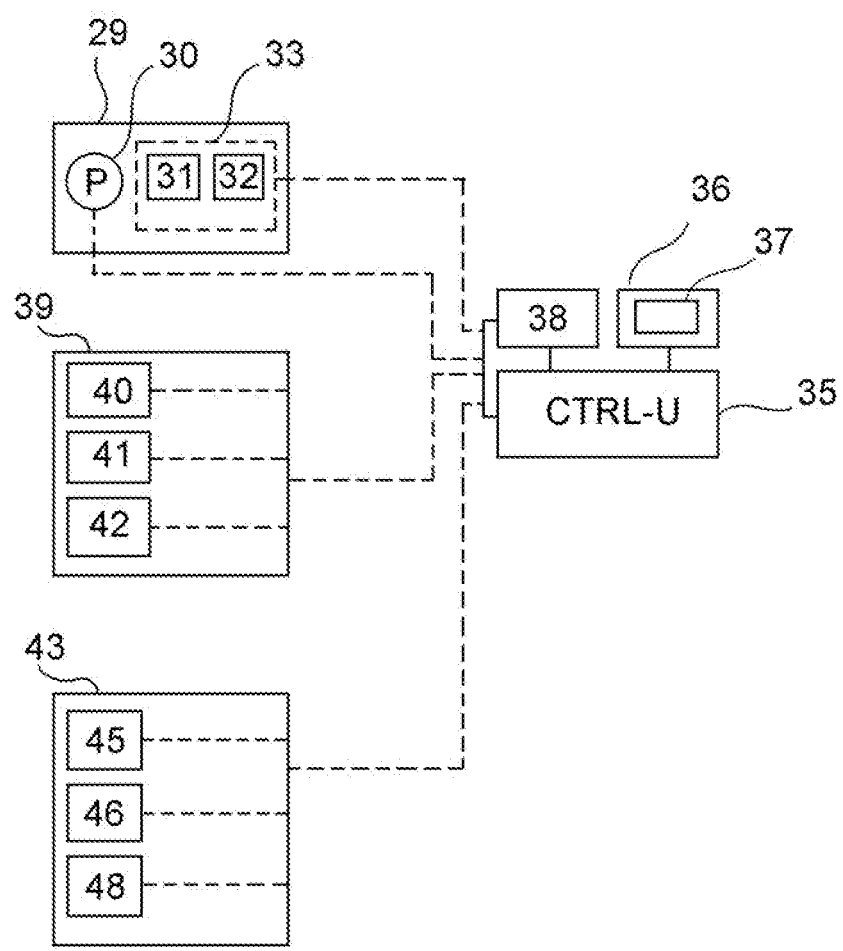

FIGS. 10, 11, 12, 13, 14, 15 show the simulation device according to an embodiment in radial section with respect to the longitudinal axis of the second observation chamber in a sequence of installing the injection device (FIG. 10, 11), of placing the soil sample (FIG. 11), of injecting a bentonite sheath (FIG. 12), of extracting the retaining partition wall (FIG. 13) and of treatment injecting (FIG. 14, 15), FIG. 16 diagrammatically shows a control unit and some detection and control units of the simulation device according to an embodiment.

With reference to the figures, a device 1 for simulating injections of liquid chemical substances into soils, comprising a support structure 2, a first observation chamber 3 which delimits an injectable space 4 adapted to accommodate a soil sample 5, a second observation chamber 6 which delimits a perforation space 7 adapted to accommodate at least one stretch of an injection device 8 for injecting chemical substances, e.g. a grouting pipe, with longitudinal extension along a longitudinal axis 9 of the second observation chamber 6, wherein the first observation chamber 3 and the second observation chamber 6 are connected to the support structure 2 and are directly bordering each other in an interface area 10, wherein the first observation chamber 3 extends from the interface area 10 in radial direction with respect to the longitudinal axis 9, and is delimited by a first containment wall 11, wherein the second observation chamber 6 extends from the interface area 10 in direction opposite to the extension of the first observation chamber 3, and is delimited by a second containment wall 12, a retaining partition wall 13 which can be inserted in an inserted position (FIG. 12) in said interface area 10 so as to separate the injectable space 4 from the perforation space 7 and to prevent the falling of part of the soil sample 5 from the first observation chamber 3 into the second observation chamber 6, and extractible or removable from the inserted position to an extracted position (FIG. 13) outside the interface area 10 so as to put the perforation space 7 in communication with the injectable space 4 in the interface area 10, one or more first transparent portions 15 formed in the first containment wall 11 and extending from a connecting area 14 between the first observation chamber 3 and the second observation chamber 6 away from the longitudinal axis 9 for viewing in real time a propagation of the chemical substance injected into the soil sample 5 by means of the injection device 8.

The simulation device 1 thus configured allows an experimental simulation of injection processes of soils in conditions very close to reality, with greatly reduced dimensions, with the possibility of verification by viewing in real time, as well as ease of repetition and variation of injection parameters at very low cost.

According to an embodiment, the device 1 further comprises one or more second transparent portions 16 formed in the second containment wall 12 and extending from the connection region 14 between the first observation chamber 3 and the second observation chamber 6 away from the interface region 10 and circumferentially about the longitudinal axis 9 for viewing the perforation space 7 and/or of the injection device 1 installed therein in real time, in particular for viewing a valve 17 of a grouting pipe 18, and/or of a sheath 19 injected into at least one part of the perforation space 7 adjacent to the interface region 10.

According to an embodiment, the first and second transparent portions 15, 16 are configured as windows directly facing towards the outside of the device 1 for a direct viewing to the naked eye or by means of cameras from the outside of the first observation chamber 3.

Additionally or alternatively, indirect viewing display devices 48, e.g. one or more cameras, optical sensors or spectrometers, for an indirect viewing of the propagation of the injected chemical substance, can be associated with the first and/or second transparent portions 15, 16. In this embodiment, it is not essential for the transparent portions 15, 16 to be directly facing towards the outside of the device 1 and can be inspected by direct vision by an operator.

According to an embodiment, the device 1 comprises a dividing septum 20 which can be installed in the second observation chamber 6, preferably in pressure-tight manner between the second containment wall 12 and the injection device 8 along the whole longitudinal length (in direction of the longitudinal axis 9) of the second observation chamber 6 so as to divide the perforation space 7 outside the injection device 8 in a first partial space 21 facing the interface area 10 and a second partial space on the opposite side and isolated with respect to the interface area 10. The first partial space 21 may be filled with a layer of sheath 19, e.g. made of bentonite or other cementitious mortar chosen for the experimental simulation, while the second partial space 22 can remain free from the injected chemical/cement substance (e.g. by filling with water and pressure-tight closing) or may be freed from it (e.g. by rinsing) to allow viewing the injection device 8 and the operation of the valves 17 during and after the steps of simulated injecting.

Description Of The First Observation Chamber 3

According to an embodiment, the first observation chamber 3 is shaped as:
- a segment of cylindrical ring with middle axis coinciding with the longitudinal axis 9 of the observation chamber 6, or
- a polyhedron with two equal trapezoidal-shaped bases preferably parallel to each other and orthogonal to the longitudinal axis 9.

The first observation chamber 3 is delimited:
- on a radially inner side, by the interface area 10 and by the retaining partition wall 13 in its inserted position,
- on a radially outer side, by the peripheral wall 23 of the first containment wall
- on a lower side, by a lower, preferably horizontal, wall 49 of the first containment wall 11,
- on an upper side, by a, preferably horizontal, upper wall 50 of the first containment wall 11,
- on the two lateral sides, by two erected side walls 51 of the first containment wall 11, which are preferably vertical, and preferably extend in substantially radial planes with respect to the longitudinal axis 9.

Advantageously, the two lateral walls 51 are transparent, e.g. made of Plexiglas or transparent polycarbonate, to achieve the first transparent portions 15.

Advantageously, the peripheral wall 23 is also transparent, e.g. made of Plexiglas or transparent polycarbonate, to further improve the viewing of the soil sample 5 in the injectable space 4.

According to an embodiment, the lower 49 and upper 50 walls can be made of metal, e.g. aluminum, to provide a stable support for fixing the transparent lateral 51 and peripheral 23 walls.

The peripheral wall 23 is a double-wall structure and advantageously forms an inner perforated wall 52 permeable to liquids, an outer wall 53 impermeable to liquids, and a gap between the inner wall 52 and the outer wall 53 for the evacuation of liquids which have permeated through the inner wall 52.

The angular opening of the first observation chamber 3 between the two side walls 51 is equal to or less than 270°, preferably lower than or equal to 90°, even more preferably equal to or less than 45°.

Description Of The Second Observation Chamber 6

According to an embodiment, the second observation chamber 6 has a tubular or preferably cylindrical shape, coaxial with the longitudinal axis 9.

The second observation chamber 6 is delimited:
- on a side facing the first observation chamber 3, by the interface area 10 and by the retaining partition wall 13 in its inserted position,
- laterally by an upright, preferably vertical, tubular wall 54, which is interrupted in the interface area 10,
- on a lower side, by a, preferably horizontal, lower wall 55,
- on an upper side, by a, preferably horizontal, upper wall 56,
wherein the tubular 54, lower 55 and upper 56 walls form part of the second containment wall 12.

Advantageously, at least part of the tubular walls 54 is transparent, e.g. made of Plexiglas or transparent polycarbonate, to make the second transparent portions 16.

According to an embodiment, the lower 55 and upper 56 walls can be made of metal, e.g. aluminum, to provide a stable support for fixing the tubular wall 54 which is at least in part or completely transparent.

According to an embodiment, the upper wall 56 of the second observation chamber 6 forms an opening 57 which can be closed by means of a cover 28 for inserting and extracting the retaining partition wall 13. Wth further advantage, the lower wall 55 of the second observation chamber 6 forms one or more centering portions, e.g. conical protrusions 64, for a correct positioning of the retaining partition wall 13 in the inserted position.

The retaining partition wall 13 itself has a wall in the shape of a cylindrical wall or planar sector, adapted to separate the first observation chamber 3 from the second observation chamber 4 in the interface area 10, as well as an upper grip portion 61, e.g. a hook or a gripping ring, to facilitate the extraction of the retaining partition wall 13 against the friction resistance with the sheath 19 and the soil sample 5.

One or both lower wall 55 and upper wall 56 of the second observation chamber 6 form a passage and centering opening 58 for the injection device 8, in particular for a grouting pipe.

Furthermore, the second containment wall 12, preferably its upper wall 56, may form an auxiliary filling inlet 59 (which can be closed) in order to fill the gap left in the sheath layer 60 after the extraction of the retaining partition wall 13.

Description Of The Dividing Septum 20

According to an embodiment, the dividing septum 20 may comprise two elongated profiles 62, e.g. made of aluminum, each having a radially outward side provided with an elastomeric seal 60 and with holes for screwing the dividing septum 20 against the tubular wall 54, a radially inner side intended to engage the injection device 8, as well as lateral sides with additional holes for screwing metal bands 63 for mounting the two profiles 62 in diametrically opposite positions on the outer surface of the injection device 8.

Description Of The Support Structure 2

The supporting structure 2 comprises:
- a supporting base 65, e.g. formed by a plurality of horizontal support beams,
- a plurality of spacer columns 66, e.g. adjustable in height, which support (the lower walls of) the observation chambers 3, 6 at a vertical distance from the supporting base 65,
- a frame 67 which supports, stiffens and mutually connects the first and second observation chambers 3, 6.

By virtue of the spacer columns 66, the observation chambers 3, 6 are positioned at a distance from the soil or from the support surface on which the device 1 rests (e.g. in a workshop or on site), protecting the observation chambers 3, 6 from damage or scratches and allowing access to the observation chambers 3, 6 from below, e.g. for positioning sensors or testing tools.

Description Of Tthe First and Second Discharge Systems

According to an embodiment, the first observation chamber 3 comprises a first discharge system 24 with a first discharge duct 25 for discharging excess liquid at a peripheral wall 23 of the first containment wall 11 opposite to (and more remote from) the interface area 10. Advantageously, the first discharge duct 25 opens into the gap between a perforated inner wall 52 and an impermeable outer wall 53 of the double-wall peripheral wall 23.

This allows a propagation of the chemical substance injected in radial direction with respect to the longitudinal axis 9 of the injection device 8 similar to the real conditions in a soil without delimited boundary.

According to an embodiment, the second observation chamber 6 comprises a second discharge system 26 with a second discharge duct 27 for discharging liquid from the perforation space 7, in particular from the second partial space 22, at a lower wall 55 of the second containment wall 12.

This allows filling, emptying and rinsing, as required (of at least the second partial space 22) of the perforation space 7, aimed at achieving a better viewing of the injection device 8, of its valve 17 and of its operation during the injection simulation.

Description Of The Injection Unit 29

According to an embodiment, the simulation device comprises an injection unit 29 with an injection pump 30 which can be connected to a source of fluid to be injected, in particular a chemical/cement substance or water, an injection duct 34 to connect the injection pump 30 to the injection device 8.

The injection unit 29 or the device 1 comprises an injection detection unit 33 with one or more injection quantity detectors, e.g. one or more of:
- a pressure sensor 31 arranged at the injection pipe 34 and adapted to detect an injection pressure (liquid pressure) in the injection pipe 34,
- a detector 32 of the flow rate (volume per unit of time) or of the volume of the injected liquid, e.g. a flow meter connected to the injection pump 30 or to the injection duct 34,
- a volume- or level detector connected to the source of liquid.

This allows a monitoring of the injection quantities, more specifically of the injection pressure, the injection flow rate and the total injected substance volume in real time during the injection simulation.

The injection pump 30 can be actuated according to simulation parameters of an injection program and of detected injection quantities, more particularly of pressure and/or flow rate and/or volume values of the injected liquid detected by means of the pressure and/or flow rate and/or volume sensors 31, 32.

This allows an adjustment of the injection pressure, the injection flow rate and the total injected substance volume in real time during the injection simulation.

The actuation of the injection pump 30 may be manual or automatic.

Description Of The Discharge Detection Unit 39

According to an embodiment, the simulation device comprises a discharge detection unit 39 with one or more discharge value detectors, e.g. one or more of:
- a detector 40 of the flow rate (volume per unit of time) or of the volume of liquid discharged by means of the first discharge system 24, e.g. a flow meter connected to the first discharge duct 25 and/or,
- a volume or level detector connected to a collection tank of the first discharge system 24, and/or
- a detector 42 of composition parameters of the liquid discharged by means of the first discharge system 24, e.g. an optical turbidity sensor, a filter, or a chemical mixture component concentration analysis device, connected to the first discharge duct 25 or to a collection tank of the first discharge system 24,
- a detector 41 of the flow rate (volume per unit of time) or of the volume of liquid discharged by means of the second discharge system 26 connected to the second discharge duct 27, and/or
- a volume or level detector connected to a collection tank of the second discharge system 26.

This allows a detection and/or a monitoring, e.g. in real time, of characteristic values of liquids discharged from the first observation chamber 3 and/or from the second observation chamber 6, more specifically of the flow rate of the discharged liquids and the total volume of discharged liquids, and the concentration of mixed components in the discharged liquids, providing useful indications on the propagation and distribution, as a function of time, of the concentration of chemical substances injected into the volume of the soil sample 5.

Description Of The Sample Monitoring Unit 43

According to an embodiment, the simulation device 1 comprises a sample monitoring unit 43 which can comprise:
one or more testing tools 45 and/or monitoring sensors 46 for monitoring and/or experimentally verifying quantities indicating the effect of the injection on the soil sample 5, and/or
one or more inspection inlets 44 formed in the first containment wall 11, preferably in the upper wall 50 and/or in the lower wall 49, but also possibly in one or both of the lateral walls 51.

Each inspection inlet 44 is configured to receive, e.g. removably and replaceably, and/or to allow the passage of:
- one or more testing tools 45 for performing experimental tests of the soil sample 5 in the first observation chamber 3,
- one or more monitoring sensors 46 for detecting quantities indicating the effect of the injection on the soil sample 5.

The inspection inlets 44 may have a closing system, preferably sealed, e.g. a plug, a door or a membrane, adapted to close the inspection inlets which are not currently occupied by testing tools 45 or monitoring sensors 46.

The sample monitoring unit 43 can also comprise testing tools 45 and/or monitoring sensors 46 which can be positioned or located within the injectable space 4, wherein said testing tools 45 and/or monitoring sensors 46 do not require the above inspection inlets 44 and can be fixed to the first containment wall 11 or simply freely positioned inside of the soil sample 5 during placement of the soil sample 5 in the first observation chamber 3.

The sample monitoring unit 43, in particular the monitoring sensors 46, also comprise the aforesaid indirect viewing means 48.

Advantageously, the inspection inlets 44 are positioned in a plurality of different radial distances, e.g. at constant radial pitch, from the longitudinal axis 9, preferably along one or more of the radial monitoring lines with respect to the longitudinal axis 9.

This allows a monitoring and/or an experimental testing of the quantities indicating the effect of the injection on the soil sample 5, both in real time and at the end of given steps of injection, in the desired radial direction of propagation of the injected chemical/cement substance.

Similarly, the testing tools 45 and/or the monitoring sensors 46 independent from the inspection inlets 44 (or in the embodiments without inspection inlets 44) may also be positioned, e.g. with a constant pitch, along one or more radial monitoring lines with respect to the longitudinal axis 9.

The radial monitoring lines can be arranged on a plurality of monitoring planes orthogonal to the longitudinal axis 9 (e.g. with constant longitudinal distance) and/or in a plurality of monitoring planes radial with respect to the longitudinal axis 9 (e.g. with constant angular pitch).

This allows a three-dimensional mapping of the indicative quantities of the effect of the injection on the soil sample 5 and of their variation over time.

In accordance with embodiments, the testing tools 45 and the monitoring sensors 46 may comprise at least one or more of:
- an electric conductivity sensor for detecting the electric conductivity and/or local water saturation in the soil sample 5,
- a mechanical extraction instrument constituted by possibly hollow cylindrical bars of small size adapted to measure the resistance of the soil treated in the sample 5; such instrument is based on the principle that the resistance to extraction increases with the increase of the degree of cementing and of the entity of the cementing bonds formed between the soil granules,
- a permeameter adapted to determine the variation of the local permeability in the soil sample 5 in relation to the degree of cementing and formation of bonds achieved; such instrument may comprise pipes or hollow bars entering into the soil sample which allow measuring the permeability, e.g. with known techniques (permeability at constant load/variable and/or gas),
- a temperature sensor for detecting the local temperature in the soil sample 5,
- an optical sensor to detect local movements and/or optical variations in the soil sample 5, e.g. a propagation speed of the injected substance,
- a pressure sensor adapted to detect the pressure of the interstitial fluids and the chemical/cement mixture injected,
- a resistivity sensor for detecting the resistivity of the soil and/or its evolution over time in relation to the interstitial fluids and to the injected chemical/cement mixture; from such information it is possible to infer the water content in the sample,
- a chemical composition sensor adapted to assess the concentration of the chemical/cement mixture at a different distances from the injection point.

Description Of The Control Unit 35

The simulation device 1 may comprise a central control unit or a plurality of distributed control circuits (generally indicated as control unit 35) in connection with a communication interface 38 (keyboard, data connection with communication protocol, wired or wireless).

The control unit 35 may be configured for inserting or receiving one or more parameters of an injection simulation program and to process the injection simulation program parameters.

By way of example, the parameters of the injection simulation program may comprise one or more of:

Parameters of the Soil Sample 5:
- material,
- particle size,
- permeability,
- water saturation,
- relative density,
- emptiness index,
- porosity,
- geo-mechanical parameters in drained and undrained conditions, Injection Parameters:
- injection pressure according to time,
- injection intervals according to time,
- pause intervals between injection intervals according to time, Technical Features of the Injection Device 8:
- pipe diameter,
- type of injection valve,
- material of the pipe,
- features of the injection valve, Chemical and/or Physical Properties of the Injected Liquid:
- initial viscosity of the injection mixture and its evolution over time,
- temperature of the chemical/cement mixture
- cure time,
- color and its changes in order to increase the contrast thereof with the soil,
- density,
- mixability with water,
- chemical reaction, e.g. in relation to the mineralogical, grain size and geo-mechanical properties of the soil to be treated, According to an embodiment, the control unit 35 can be (also) in signal connection with one, more or all of the detectors and sensors of the injection detection unit 33 and configured to receive and process the respective injection pressure, injection flow rate and total injection volume signals supplied by sensors 31, 32.

According to an embodiment, the control unit 35 may (also) be in signal connection with one, more or all of the detectors 40, 41, 42 of the discharge detection unit 39 and configured to receive and process the respective flow rate, volume, turbidity, concentration signals supplied by the detectors 40, 41, 42.

According to an embodiment, the control unit 35 may (also) be in signal connection with one, more or all testing tools 45 and monitoring sensors 46 of the sample monitoring group 43 and configured to receive and process the respective signals indicating the effect of the injection on the soil sample 5, supplied by the testing tools 45 and by the monitoring sensors 46.

In an embodiment, the injection pump 30 may be connected to and controlled by the control unit 35 as a function of the parameters of the injection simulation program and possibly (also) of one or more of the injection pressure, injection flow rate and injection total volume signals supplied by sensors 31, 32.

According to an embodiment, the control unit 35 is in signal connection, wired or wireless, or adapted to connect with a memory 36 containing a database 37 (e.g. forming but not necessarily part of the simulation device 1) and configured to store in the database 37:
- the parameters of the injection simulation program, and/or
- the experimental values (and possibly their variation over time) of the detected injection magnitudes, e.g. the pressure and/or flow and/or injection volume values detected by the pressure 31, flow rate and/or volume 32 sensors, possibly as a function of time, and/or the experimental values (and possibly their variation over time) of the discharge quantities detected by the injection detection group 39, e.g. the discharge liquid flow rate value and the total discharged liquid volume value and the concentration of the mixed components in the discharged liquids, detected by the detectors 40, 41, 42, and/or the experimental values (and possibly their variation over time) of the quantities indicative of the effect of the injection on the soil sample 5, detected by means of testing tools 45 and monitoring sensors 46, as well as their associations and/or correlations.

As a function of the experimental values stored and/or related with the parameters of the injection simulation program, it is possible and envisaged to select the most suitable injection parameters for a given geotechnical-engineering project treatment of a soil.

Such parameters comprise, in addition to those mentioned above and applicable to the simulation, e.g. also the injection positions in situ, the distance between perforations, the type of injection device, the choice of the substance to be injected, the injection program.

The selection of the injection parameters for a given geotechnical-engineering project may be performed by the control unit 35 or by a further processing means by comparing the values (and possibly of the variation over time) of the quantities indicative of the effect of the injection on the soil sample 5 detected for a plurality of different sets of parameters of the injection program with predetermined (ranges of) reference values or target values.

Furthermore, as a function of experimental values stored and correlated with the injection simulation program parameters, it is possible and envisaged to calibrate numerical model parameters for numerical injection process simulation of soil, and in this manner to refine and experimentally validate numerical models at low cost and in conditions very close to reality.

Description Of The Injection Simulation Method

The invention further relates to a method for simulating injections of liquid chemical/cement substances into soils, comprising an injection simulation through the steps of:
preparing a simulation device 1 according to one of the described embodiments,
preparing a soil sample 5 having chosen properties,
placing the soil sample 5 in the first observation chamber 3 of the simulation device 1,
preparing an injection device 8, e.g. a grouting pipe 18, having chosen properties,
installing the injection device 8 in the second observation chamber 6 of the simulation device 1,
carrying out an injection program of the chemical/cement substance by means of the injection device 8 installed in the second observation chamber 6,
viewing in real time in the soil sample 5 a propagation of the chemical/cement substance injected by means of the injection device in the soil sample 8, through the one or more first transparent portions 15 in the first containment wall 11 of the first observation chamber 3.

The method may further comprise one or more repetitions of the injection simulation, by varying one or more of the aforesaid parameters of the injection program simulation.

This allows an optimization of the injection parameters for specific needs and treatment project conditions of a soil.

The further steps of the method have been already described with reference to the simulation device 1 and will not be repeated here for the sake of brevity. Such further steps of method, described above as being executed or as executable by the simulation device 1 or by means of functional units of the simulation device 1, may be carried out even by technical means different from those described with reference to device 1, or manually.

The invention further relates to a method for defining or optimizing an engineering-geotechnical project for the treatment/consolidation of selected soil by injecting chemical/cement substances, comprising the steps of:
carrying out the aforesaid simulation injection method with one or more soil samples 5 prepared according to the properties of the selected soil,
selecting injection parameters for the treatment/consolidation of the soil chosen as a function of the values (and possibly of their variation over time) of the quantities indicative of the effect of the injection on the prepared soil samples 5, detected e.g. but not necessarily by means of testing tools 45 and monitoring sensors 46.

The invention further relates to a method for executing a treatment/consolidation of a selected soil by injecting chemical/cement substances, comprising the steps of:
carrying out the aforesaid simulation injection method with one or more soil samples 5 prepared according to the properties of the selected soil,
performing the treatment/consolidation of the soil chosen by means of injection parameter selected as a function of the values (and possibly of their variation over time) of the quantities indicative of the effect of the injection on the prepared soil samples 5, e.g. detected but not necessarily by means of the testing tools 45 and monitoring sensors 46.

The preparation of the soil sample 5 may comprise taking the sample from a chosen soil and/or reconstructing or making the sample according to a recipe, on the basis of the soil parameters already described previously, namely:
material,
particle size,
permeability,
water saturation,
relative density,
emptiness index,
porosity,
geo-mechanical parameters in drained and undrained conditions, According to an advantageous aspect of the invention, the device 1 is configured to (and the method envisages) executing injection simulations in scale 1:1, thus with:
a real injection device 8 and/or
with a size and shape of the second observation chamber 6 corresponding to the diameter and shape of a real perforation,
as well as with radial and longitudinal dimensions of the first observation chamber 3 with respect to the longitudinal axis 9 corresponding to the radial and axial extension of a local injection envisaged in design.

General Definitions Applicable to the Present Description

The injection fluids are water, cement mixtures, chemical mixtures (in the future could also be resins).

The sheath mixture is a cement mixture typically containing bentonite;

in general, the concerned injections relate to mixtures (consisting of cement, water, and often chemical additives and bentonite; or by chemical reagents and water).

Obviously, a person skilled in art may make further changes and variants to the injection simulation device and method, all contained within the scope of protection of the invention as defined in the following claims, in order to satisfy contingent needs and specifications.

The invention claimed is:

1. A device for simulating injections of liquid chemical substances into soils, comprising:
   a support structure,
   a first observation chamber which delimits an injectable space which receives a soil sample,
   a second observation chamber which delimits a perforation space which houses at least one stretch of an injection device for injecting the liquid chemical substances, with longitudinal extension along a longitudinal axis of the second observation chamber,
   wherein the first observation chamber and the second observation chamber are connected to the support structure and are directly bordering to each other in an interface area,
   wherein the first observation chamber extends from the interface area in radial direction with respect to the longitudinal axis, and is delimited by a first containment wall,
   wherein the second observation chamber extends from the interface area in direction opposite to the extension of the first observation chamber, and is delimited by a second containment wall,
   a retaining partition wall insertable in an inserted position in said interface area so as to separate the injectable space from the perforation space and to prevent the falling of material of the soil sample from the first observation chamber into the second observation chamber, and extractable from the inserted position to an extracted position outside the interface area so as to put the perforation space in communication with the injectable space in the interface area,
   one or more first transparent portions formed in the first containment wall and extending from a connecting area between the first observation chamber and the second observation chamber away from the longitudinal axis for viewing in real time a propagation of the chemical substance injected into the soil sample by means of the injection device.

2. The device according to claim 1, further comprising one or more second transparent portions formed in the second containment wall and positioned circumferentially about the longitudinal axis for viewing in real time of the perforation space and/or of the injection device therein installed.

3. The device according to claim 1, wherein indirect visualization devices are associated with the transparent portions.

4. The device according to claim 1 comprising a dividing septum which can be installed in the second observation chamber between the second containment wall and the injection device along the whole longitudinal length in direction of the longitudinal axis of the second observation chamber so as to divide the perforation space outside the injection device in a first partial space facing the interface area and a second partial space on the opposite side and isolated with respect to the interface area,
   said first partial space being fillable with a layer of sheath and said second partial space being fillable with water and rinsable for viewing the injection device and the operation of the valves thereof.

5. The device according to claim 1, wherein the first observation chamber has a shape of:
   a segment of cylindrical ring with middle axis coinciding with the longitudinal axis, or
   a polyhedron with two equal trapezoidal-shaped bases preferably parallel to each other and orthogonal to the longitudinal axis,
   wherein an angle between the two side walls is equal to or less than 270°, or equal to or less than 90°, or equal to or less than 45°.

6. The device according to claim 1, wherein the first observation chamber is delimited:
   on a radially inner side, by the interface area and by the retaining partition wall in the inserted position,
   on a radially outer side, by a peripheral wall of the first containment wall,
   on a lower side, by a lower horizontal wall of the first containment wall,
   on an upper side, by a, preferably horizontal, upper, wall of the first containment wall,
   on two lateral sides, by two erected side walls of the first containment wall, which are preferably vertical, and preferably extend in substantially radial planes with respect to the longitudinal axis,
   wherein the two side walls and the peripheral wall are transparent.

7. The device according to claim 1, wherein:
   a peripheral wall of the first observation chamber is a double-wall structure with an inner perforated wall permeable to liquids, an outer wall impermeable to liquids, and a gap between the inner wall and the outer wall for the evacuation of liquids which have permeated through the inner wall.

8. The device according to claim 1, wherein the second observation chamber has a tubular or cylindrical shape coaxial with the longitudinal axis, and is delimited:
   on a side facing the first observation chamber, by the interface area and by the retaining partition wall in the inserted position,
   laterally by an upright tubular wall of the second containment wall that is interrupted in the interface area,
   on a lower side, by a lower horizontal wall of the second containment wall,
   on an upper side, by an upper horizontal wall of the second containment wall,
   wherein at least part of the tubular wall is transparent and at least one of the lower and upper walls form a passage and centering opening for the injection device.

9. The device according to claim 1, wherein:
   an upper wall of the second observation chamber forms an opening which is closable by means of a cover, for the insertion and extraction of the retaining partition wall, and
   a lower wall of the second observation chamber forms one or more centering portions for a correct positioning of the retaining partition wall in its inserted position.

10. The device according to claim 1, wherein the retaining partition wall has a wall shaped like a sector of cylindrical wall and an upper annular grip portion for facilitating the extraction of the retaining partition wall.

11. The device according to claim 1, wherein an upper wall of the second containment wall forms an auxiliary filling inlet for filling a gap left after the extraction of the retaining partition wall.

12. The device according to claim 1, wherein the first observation chamber comprises a first discharge system with a first discharge duct for discharging excess liquid at a peripheral wall of the first containment wall remote from the interface area.

13. The device according to claim 1, wherein the second observation chamber comprises a second discharge system with a second discharge duct for discharging liquid from the perforation space at a lower wall of the second containment wall.

14. The device according to claim 1, comprising an injection unit with an injection duct for connecting an injection pump to the injection device, and also an injection detection unit with one or more injection value detectors selected in the group consisting of:
- a pressure sensor arranged at the injection pipe and adapted for detecting an injection pressure in the injection pipe,
- a detector of the flow rate or of the volume of injected liquid, connected to the injection pipe.

15. The device according to claim 12, comprising a discharge detection unit with one or more discharge value detectors selected in the group consisting of:
- a detector of the flow rate or of the volume discharged by means of the first discharge system,
- a volume or level detector connected to a collection tank of the first discharge system,
- a detector of parameters of the composition of the liquid discharged by means of the first discharge system connected to the first discharge duct or to a collection tank of the first discharge system,
- a detector of the flow rate or of the volume of liquid discharged by means of the second discharge system connected to the second discharge duct, a volume or level detector connected to a collection tank of the second discharge system.

16. The device according to claim 1, comprising a sample monitoring unit for performing experimental tests on the soil sample and for detecting values indicative of the effect of the injection on the soil sample in the first observation chamber, said sample monitoring unit comprising one or more devices selected in the group consisting of:
- experimental testing instruments,
- monitoring sensors,
- inspection inlets formed in the first containment wall and configured for the insertion of testing instruments and monitoring sensors.

17. The device according to claim 16, wherein the sample monitoring unit comprises one or more of:
- an electric conductivity sensor for detecting the electric conductivity and/or local water saturation in the soil sample,
- a mechanical extraction instrument adapted to measure the resistance to extraction of the soil in the sample,
- a permeameter for determining the hydraulic conductivity in the soil sample,
- a temperature sensor for detecting the local temperature in the soil sample,
- an optical sensor adapted to detect movements and/or local optical variations in the soil sample,
- a pressure sensor adapted to detect the pressure of the interstitial fluids and the chemical/cement mixture injected,
- a resistivity sensor for detecting the resistivity of the soil,
- a chemical composition sensor adapted for assessing the local concentration of the chemical/cement mixture in the soil sample.

18. The device according to claim 14, comprising a control unit connected with a communication interface and configured to receive and process parameters of an injection simulation program selected in the group consisting of:
parameters of the soil sample:
  material,
  particle size,
  permeability,
  water saturation,
  relative density,
  emptiness index,
  porosity,
  geo-mechanical parameters in drained and undrained conditions,
injection parameters:
  injection pressure according to time,
  injection intervals according to time,
  pause intervals between injection intervals according to time,
technical parameters of the injection device:
  tube diameter,
  type of injection valve,
  features of the injection valve,
chemical and physical parameters of the injected liquid:
  initial viscosity of the injection mixture and its evolution over time,
  temperature of the chemical/cement mixture
  cure time,
  color and its changes in order to increase the contrast thereof with the soil,
  density,
  mixability with water,
  chemical reaction for curing in relation to the mineralogical, grain size and geo-mechanical properties of the soil to be treated,
wherein the control unit is in signal connection with the injection detection unit and is configured to receive and process signals of said injection quantities,
wherein the control unit is in signal connection with the discharge detection unit and is configured to receive and process signals of said discharge quantities,
wherein the control unit is in signal connection with the sample monitoring unit and is configured to receive and process signals of said quantities indicative of the effect of the injection on the soil sample,
wherein the control unit is adapted to be connected to a memory containing a database and configured to save in the database:
the parameters of the injection simulation program,
detected values of the injection quantities,
detected values of the discharge quantities,
values of the quantities indicative of the effect of the injection on the soil sample, and also the correlations thereof.

19. A method for simulating injections of liquid chemical or cement substances into soils, comprising an injection simulation through the steps of:
preparing a simulation device for simulating injections of liquid chemical substances into soils, said simulation device comprising:
a support structure,
a first observation chamber which delimits an injectable space which receives a soil sample,
a second observation chamber which delimits a perforation space suitable for housing which houses at least one stretch of an injection device for injecting the liquid chemical substances, with longitudinal extension along a longitudinal axis of the second observation chamber, wherein the first observation chamber and the second observation chamber are connected to the support structure and are directly bordering to each other in an interface area, wherein the first observation chamber extends from the interface area in radial direction with respect to the longitudinal axis, and is delimited by a first containment wall, wherein the second observation chamber extends from the interface area in direction opposite to the extension of the first observation chamber, and is delimited by a second containment wall, a retaining partition wall insertable in an inserted position in said interface area so as to separate the injectable space from the perforation space and to prevent the falling of material of the soil sample from the first observation chamber into the second observation chamber, and extractable from the inserted position to an extracted position outside the interface area so as to put the perforation space in communication with the injectable space in the interface area, one or more first transparent portions formed in the first containment wall and extending from a connecting area between the first observation chamber and the second observation chamber away from the longitudinal axis for viewing in real time a propagation of the chemical substance injected into the soil sample by means of the injection device, preparing a soil sample having properties selected according to simulation parameters, placing the soil sample in the first observation chamber of the simulation device, preparing an injection device having properties selected according to simulation parameters, installing the injection device in the second observation chamber of the simulation device, carrying out an injection program of the chemical/cement substance by means of the injection device installed in the second observation chamber according to simulation parameters, viewing in real time a propagation of the injected chemical/cement substance in the soil sample, through the one or more first transparent portions of the first observation chamber.

20. The method according to claim 19, comprising one or more repetitions of the injection simulation with varying said simulation parameters.

21. The method according to claim 20, comprising the steps of:
carrying out the method with soil samples prepared according to the properties of a selected soil,
selecting injection parameters for treating the selected soil according to values of parameters indicative of the effect of the injection on the prepared soil samples, detected by means of the injection simulations,
defining an engineering-geotechnical project for the treatment of said selected soil by injecting the liquid chemical or cement substances.

22. The method according to claim 20, comprising the steps of:
carrying out the method with soil samples prepared according to the properties of a selected soil,
carrying out a treatment of the selected soil by means of injection parameters selected according to values of parameters indicative of the effect of the injection on the prepared soil samples, detected by means of the injection simulations.

* * * * *